United States Patent [19]

Klaus

[11] Patent Number: 4,808,631

[45] Date of Patent: Feb. 28, 1989

[54] AROMATIC ACID DERIVATIVES

[75] Inventor: Michael Klaus, Weil am Rhein, Fed. Rep. of Germany

[73] Assignee: Hoffmann-La Roche Inc., Nutley, N.J.

[21] Appl. No.: 108,337

[22] Filed: Oct. 14, 1987

[30] Foreign Application Priority Data

Nov. 7, 1986 [CH] Switzerland ................. 4438/86

[51] Int. Cl.[4] ......................................... A61K 31/195
[52] U.S. Cl. .................................................. 514/561
[58] Field of Search ............................ 514/561, 563

[56] References Cited

FOREIGN PATENT DOCUMENTS 0170105 2/1980 European Pat. Off. .

OTHER PUBLICATIONS

Chem. Pharm. Bull., 32 4212 (1984).

Primary Examiner—Stanley J. Friedman
Attorney, Agent, or Firm—Jon S. Saxe; Bernard S. Leon; William G. Isgro

[57] ABSTRACT

Use of compounds of the formula

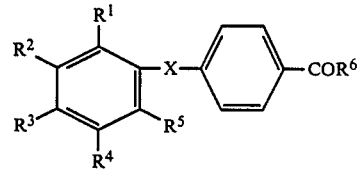

wherein $R^1$, $R^2$, $R^3$, $R^4$ and $R^5$, independently are hydrogen, alkyl, or $C_{3-7}$-cycloalkyl or two adjacent residues $R^1$ to $R^5$ taken together with adjacent carbons of the phenyl ring form a 5- to 7-membered ring optionally substituted by one or more lower alkyl groups; X is $-NR^7-CO-$ or $-CO-NR^7-$; $R^6$ is hydroxy, lower-alkoxy or $-NR^8R^9$; and $R^7$, $R^8$ and $R^9$, independently, are hydrogen or lower-alkyl, and where $R^6$ is hydroxy, their pharmaceutically usable salts, for the treatment of inflammatory and rheumatic diseases.

3 Claims, No Drawings

AROMATIC ACID DERIVATIVES

BRIEF SUMMARY OF THE INVENTION

The invention comprises the finding that compounds of the formula

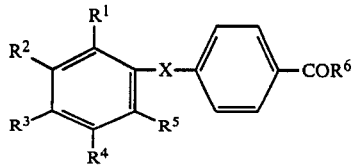

wherein $R^1$, $R^2$, $R^3$, $R^4$ and $R^5$, independently, are hydrogen, alkyl, or $C_{3-7}$-cycloalkyl or two adjacent $R^1$ to $R^5$ groups taken together with the adjacent carbons of the phenyl ring form a 5 to 7-membered ring optionally substituted by one or more lower alkyl groups; X is $-NR^7-CO-$ or $-CO-NR^7-$; $R^6$ is hydroxy, lower-alkoxy or $-NR^8R^9$; and $R^7$, $R^8$ and $R^9$, independently, are hydrogen or lower-alkyl, and, when $R^6$ is hydroxy, their pharmaceutically acceptable salts are useful for the treatment of inflammatory and rheumatic diseases.

The invention is accordingly concerned with the compounds of formula I and pharmaceutically acceptable salts of carboxylic acids of formula I for use in the treatment of such diseases and for the preparation of medicaments for the treatment of inflammatory and rheumatic diseases.

DETAILED DESCRIPTION OF THE INVENTION

The invention comprises the finding that compounds of the formula

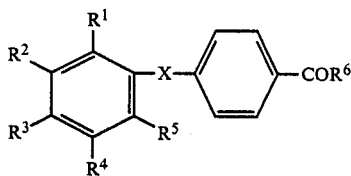

wherein $R^1$, $R^2$, $R^3$, $R^4$ and $R^5$, independently, are hydrogen, alkyl, or $C_{3-7}$-cycloalkyl or two adjacent $R^1$ to $R^5$ groups taken together with the adjacent carbons of the phenyl ring form a 5 to 7-membered ring optionally substituted by one or more lower alkyl groups; X is $-NR^7-CO-$ or $-CO-NR^7-$; $R^6$ is hydroxy, lower-alkoxy or $-NR^8R^9$; and $R^7$, $R^8$ and $R^9$, independently, are hydrogen or lower-alkyl. and, when $R^6$ is hydroxy, their pharmaceutically acceptable salts are useful for the treatment of inflammatory and rheumatic diseases.

The invention comprises a method of treating inflammatory and rheumatic diseases by administering to a warm-blooded animal in need of such treatment an effective amount of a compound of formula I or a pharmaceutically acceptable salt of a carboxylic acid of formula I, that is, a compound of formula I wherein $R^6$ is hydroxy.

Examples of inflammatory and rheumatic diseases are acute and chronic inflammations of the skin and mucous membranes, primary-chronic polyarthritis (rheumatoid arthritis), ankylosing spondylitis, osteoarthritides, arthritides and arthroses of the widest variety of joints of an inflammatory and degenerative nature.

Preferred compounds of formula I are those in which $R^2$ and $R^3$ taken together are a 5 to 7-membered ring which is substituted by lower-alkyl; or $R^2$, $R^3$ and $R^4$ are lower-alkyl, preferably tert.butyl or isopropyl, and $R^1$ and $R^5$ are hydrogen. X preferably is $-CO-NH-$ or $-NH-CO-$.

The compounds of the formula

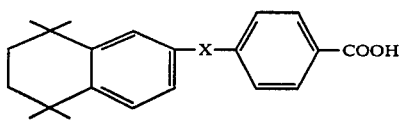

wherein X is $-NH-CO-$ or $-CO-NH-$, and their pharmaceutically acceptable salts are particularly preferred compounds of the invention.

Examplary of the compounds of formula Ia are: p-(5,6,7,8-tetrahydro-5,5,8,8-tetramethyl-2-naphthalene carboxamido)benzoic acid; and p-[(5,6,7,8-tetrahydro-5,5,8,8-tetramethyl-2-naphthyl)carbamoyl]benzoic acid.

The term "lower" denotes groups, preferably of 1–6 C-atoms, such as methyl, ethyl, propyl or methoxy, ethoxy, propoxy and the like.

Examplary of an optionally lower-alkyl-substituted 5 to 7-membered rings which are formed by two adjacent $R^1$ to $R^5$ groups taken together with the adjacent carbons of the phenyl ring are:

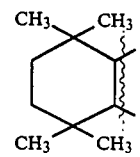

Examplary of pharmaceutical salts are, for instance, the alkali metal salts such as sodium and potassium salts; alkaline earth salts such as calciuM salts; and salts with organic amines such as triethylamine salts.

The compounds of formula I and their salts are described in European Patent Application No. A2-O 170 105 and are disclosed as active substances for the treatment of malignant diseases such as leukemia.

In accordance with the invention, the treatment with and the use of the compounds of formula I and their salts are preferably effected in preparations for systemic administration.

In the case of systemic administration, the effective amount of a compound of formula I or salt thereof varies according to the requirements of the individual patient, with a daily dosage of about 5 μg to about 500 μg, preferably about 50–100 μg, per kg body weight of a adult warm-blooded animal coming into consideration. The dosage can be administered as a single dosage or divided into several dosages.

As dosage forms, there come into consideration for systemic administration usual solid or liquid dosage forms, for example, suppositories, as solid oral dosage forms capsules, tablets, dragees, pills, powders, granulates and the like, as liquid oral dosage forms, solutions, syrups, suspensions, elixirs and the like, and as parenteral dosage forms, infusion or injection solutions which can be injected intravenously or intramuscularly. A solid dosage unit, for example, a capsule, preferably contains the active substance in amounts of 0.1 mg to 10 mg.

The activity of the compounds of formula I of the invention can be demonstrated on the basis of the following test results:

Groups of 10 male mice having a minimum weight of 20 g are sensitized on day 0 with methylated bovine serum albumin; MBSA. The sensitization is effected or two sites of the shaved ventral side by the intradermal injection of in each case 0.05 ml of a 1:1 mixture (V/V) of 0.5% MBSA and Freund's complete adjuvant. Nine (9) days later (day 8) 0.02 ml of 1% MBSA is injected subplantarly in one hind paw as a "challenge" to the experimental animals, while the same volume of a sterile sodium chloride solution is injected into the other hind paw. Twenty four (24) hours later (day 9) the inflammation is estimated on the basis of the edema brought about by the injection. The volumes of the paws are measured by water displacement plethysmography. The test compound was administered orally to the experimental animals on days 0 to 4, that is, for 5 days, and the results of the animals treated with compounds of formula Ia were compared with those of control animals treated only with the vehicle. The results were calculated as follows: the percentage increase in the paw volume after the "challenge" administration of the MBSA was calculated for each mouse according to the formula $$\frac{\text{"Challenge" paw volume minus control paw volume}}{\text{Control paw volume}} \times 100\%.$$

Thereafter, the average increase in the paw volume for each group is calculated and the percentage decrease in the paw volume of the animals treated with the test compound compared with the control animals was calculated as follows:

$$\frac{\begin{array}{c}\text{\% Increase in the paw volume}\\\text{of the control animals minus}\\\text{\% increase in the paw volume of the treated animals}\end{array}}{\text{\% Increase in the paw volume of the control animals}} \times 100\%.$$

The results are compiled hereinafter in Table I.

TABLE I

| Compound | Dosage mg/kg/day | % Inhibition of the paw edema | p < |
|---|---|---|---|
| Ia' | 0.1 | 40 | 0.01 |
| X = —CONH— | 0.3 | 63 | 0.001 |
| | 1.0 | 78 | 0.001 |
| Ia'' | 0.1 | 33 | — |
| X = —NH—CO— | 0.3 | 46 | 0.01 |
| | 1.0 | 50 | 0.01 |

In a similar manner, the activity in the Adjuvant Arthritis Test was determined. In this test female rats weighing 115–170 g are used. A suspension of heat killed M. tuberculosis in liquid paraffin is injected in the sub-plantar surface of the right hind paw of each rat thereby inducing a primary response at the injection site and a secondary response at other body parts (non-injected paws, nose, ear and tail). The test compound was administered orally as described above and the lesions were observed (Table II). Of particular interest is the suppression of the secondary systemically induced lesions.

TABLE II

| Compound | Dose mg/kg/day | % Inhibition of paw edema (a) | (b) | (c) | % Inhibition of all lesions (d) |
|---|---|---|---|---|---|
| Ia' | 0,03 | 9 | 25 | 57 | 25 |
| X = —CONH— | 0,1 | 9 | 28 | 95 | 95 |
| | 0,3 | 28 | 50 | 98 | 98 |

(a) injected paw, primary lesion (day 0–4)
(b) injected paw, secondary lesion (day 7–17)
(c) non-injected paw, secondary lesion (day 7–17)
(d) overall lesion score (scale from 0–3) of nose, ears, non-injected paws, tail The compounds of formula Ia exhibited a remarkably low A-hypervitaminosis activity; signs of a A-hypervitaminosis (Bollag, Europ. J. Cancer 10, 731 (1974)) were established only at dosages of 3 mg/kg/day.

The preparation of the above-mentioned dosage forms can be effected in the usual manner, for example, on the basis of the following Examples.

EXAMPLE 1

Hard gelatin capsules containing the following ingredients can be prepared:

| Ingredients | mg/capsule A | B |
|---|---|---|
| 1. p-(5,6,7,8-tetrahydro-5,5,8,8-tetramethyl-2-naphthalenecarboxamido) benzoic acid | 0.1 | 10.0 |
| 2. Sodium carboxymethylcellulose | 9.9 | 10.0 |
| 3. Microcrystalline cellulose | 281.0 | 271.0 |
| 4. Talc | 8.0 | 8.0 |
| 6. Magnesium stearate | 1.0 | 1.0 |
| Total | 300.0 | 300.0 |

Procedure

The active substance is homogeneously mixed with the sodium carboxymethylcellulose; this mixture is mixed with the microcrystalline cellulose, talc and magnesium stearate. The final mixture is filled into capsules of size 0.

EXAMPLE 2

Tablets containing the following ingredients can be prepared as follows:

| Ingredients | mg/tablet A | B |
|---|---|---|
| 1. p-(5,6,7,8-tetrahydro-5,5,8,8-tetramethyl-2-naphthalenecarboxamido) benzoic acid | 0.1 | 10.0 |
| 2. Lactose powd. | 130.9 | 121.0 |
| 3. Maize starch white | 30.0 | 30.0 |
| 4. Povidone K30 | 5.0 | 5.0 |
| 6. Maize starch white | 30.0 | 30.0 |
| 7. Magnesium stearate | 4.0 | 4.0 |
| Total | 200.0 | 200.0 |

Procedure

The finely ground active substance is mixed with the powdered lactose and white maize starch. The mixture is moistened with an aqueous solution of Povidone K30 and kneaded, and the resulting mass is granulated, dried and sieved. The granulate is mixed with the white maize starch (2nd portion) and the magnesium stearate and pressed to tablets of suitable size.

EXAMPLE 3

Soft gelatin capsules containing the following ingredients can be prepared as follows:

| Ingredients | mg/capsule |
| --- | --- |
| 1. p-(5,6,7,8-tetrahydro-5,5,8,8-tetramethyl-2-naphthalenecarboxamido) benzoic acid | 1.0 299.0 |
| 2. Triglyceride | 299.0 |
| Total | 300.0 |

Procedure 10 g of the active substance are dissolved in 90 g of medium-chain triglyceride with stirring, inert gasification and exclusion of light. This solution is processed as the capsule fill mass to give soft gelatin capsules containing 1 mg of active substance.

I claim:

1. A method of treatment of inflammatory and rheumatic diseases which comprises administering to a warm-blooded host in need of such treatment an effective amount of a compound of the formula

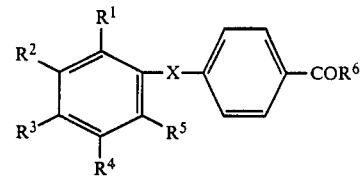

wherein $R^1$, $R^2$, $R^3$, $R^4$ and $R^5$, independently, are hydrogen, alkyl or $C_{3-7}$-cycloalkyl or two adjacent residues $R^1$ to $R^5$ taken together with the adjacent carbon atoms of the phenyl ring form a 5- to 7-membered ring optionally substituted by one or more lower alkyl groups; X is a residue —NH—CO— or —CO—NH—; $R^6$ is hydroxy, lower-alkoxy or —$NR^8R^9$; and $R^7$, $R^8$ and $R^9$, independently, are hydrogen or lower-alkyl, or, wherein $R^6$ is hydroxy, a pharmaceutically acceptable salt thereof.

2. A method, in accordance with claim 1, wherein $R^2$ and $R^3$ taken together with the adjacent carbons of the phenyl ring form a 5- to 7-membered ring substituted by one or more lower alkyl groups and X is —CO—NH— or —NH—CO—.

3. A method, in accordance to claim 1, wherein a compound of formula I has the formula

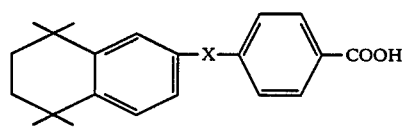

wherein X is —CO—NH— or —NH—CO—, or a pharmaceutically acceptable salt thereof.

* * * * *